US009968512B2

(12) United States Patent
Hahr et al.

(10) Patent No.: US 9,968,512 B2
(45) Date of Patent: May 15, 2018

(54) STIMULATION DEVICE

(75) Inventors: Meike Hahr, Hamburg (DE); Till Muhl, Hamburg (DE)

(73) Assignee: OVO JOINT VENTURE, LLC, Hightstown, NJ (US)

( * ) Notice: Subject to any disclaimer, the term of this patent is extended or adjusted under 35 U.S.C. 154(b) by 73 days.

(21) Appl. No.: 14/426,319

(22) PCT Filed: Sep. 7, 2012

(86) PCT No.: PCT/EP2012/067466

§ 371 (c)(1), (2), (4) Date: Feb. 4, 2016

(87) PCT Pub. No.: WO2014/037048

PCT Pub. Date: Mar. 13, 2014

(65) Prior Publication Data

US 2016/0184178 A1 Jun. 30, 2016

(51) Int. Cl.

| | |
|---|---|
| ***A61F 5/00*** | (2006.01) |
| ***A61H 19/00*** | (2006.01) |
| ***A61H 23/02*** | (2006.01) |
| *A61H 15/00* | (2006.01) |

(52) U.S. Cl.

CPC ............. *A61H 19/34* (2013.01); *A61H 19/44* (2013.01); *A61H 23/02* (2013.01); *A61H 2015/0042* (2013.01); *A61H 2201/0107* (2013.01); *A61H 2201/5035* (2013.01)

(58) Field of Classification Search

CPC ........ A61H 23/02; A61H 19/00; A61H 19/30; A61H 19/34; A61H 19/40; A61H 19/44

USPC ......................................... 600/38–41; 601/46

See application file for complete search history.

(56) References Cited

U.S. PATENT DOCUMENTS 7,717,867 B2 * 5/2010 Nan ....................... A61H 15/00 600/38
8,308,667 B2 * 11/2012 Lee ........................ A61H 19/44 600/38
8,784,345 B2 * 7/2014 Peddicord ............. A61H 19/00 601/15
2002/0188233 A1 * 12/2002 Denyes .................. A61H 19/34 601/46

FOREIGN PATENT DOCUMENTS

| | | |
|---|---|---|
| DE | 20 2009 012229 | 11/2009 |
| EP | 2364687 | 9/2011 |
| JP | 2004313690 | 11/2004 |
| JP | 2005288079 | 10/2005 |
| WO | WO2011045588 | 4/2011 |

* cited by examiner

*Primary Examiner* — John Lacyk

(74) *Attorney, Agent, or Firm* — Richard E. Oney; Tiffany & Bosco, P.A.

(57) ABSTRACT

Disclosed is a stimulation device comprising a first arm (2) having a first proximal end portion (2*a*) and a distal end portion (2*b*) adapted to be inserted into a vagina and a second arm (4) having a proximal end portion (4*a*) and a distal end portion (4*b*) adapted to get into contact with a body portion outside the vagina, wherein the first arm (2) and the second arm (4) are provided for being connected with each other at their respective proximal end portion (2*a;* 4) so as to form an essentially U- or V-shaped arrangement. According to the present invention, the stimulation device comprises coupling means (6, 10) adapted to provide a releasable connection of the first and second arms (2, 4) at their respective proximal end portion (2*a;* 4*a*).

27 Claims, 6 Drawing Sheets

STIMULATION DEVICE

The present invention relates to a stimulation device comprising a first arm adapted to be inserted into a vagina and a second arm adapted to get into contact with a body portion outside the vagina, wherein the first arm and the second arm are provided for being connected with each other at their respective proximal end portions so as to form an essentially U- or V-shaped arrangement.

A stimulation device having the aforementioned configuration as disclosed e.g. in EP 1 477 149 A1 is widely known in the prior art for a long time.

There are different types of stimulation devices having the aforementioned configuration, which types differ in function and shape. For instance, there are so-called passive stimulation devices which do not create any vibrations or rotational movements, whereas so-called active stimulation devices are designed to create vibrations and/or rotational movements in at least one of their arms. Further, there are rigid stimulation devices, or there are stimulation devices wherein at least one of their arms is flexible or elastic. Moreover, there are stimulation devices whose arms have similar dimensions, in particular are of similar length and/or thickness or diameter, whereas there are also stimulation devices whose first arm forms a long and thick inner arm and whose second arm forms a short and thin outer arm.

Preferably but not exclusively, the present invention focuses upon a particular type of stimulation device which is called "rabbit" vibrator whose first arm is a vibrating and rotating shaft made in the shape of a phallus and whose second arm forms a clitoral stimulator attached to the shaft of the first arm. The name "rabbit" is derived from the fact that the second arm forming the clitoral stimulator looks like a pair of rabbit ears when this type of stimulation device appeared on the market in the 1990s. Rabbit vibrators are designed to give more intense sensations than the more traditional dildo or clitoral stimulator, since they are provided for simultaneous internal (vaginal) and external (clitoral) stimulation.

It is an object of the present invention to improve a stimulation device having the aforementioned configuration so as to expand its application possibilities in order to be used for different pleasure in accordance with the user's current needs and, thus, to give more fun.

In order to achieve the above and further objects, according to the present invention, there is provided a stimulation device comprising a first arm adapted to be inserted into a vagina and a second arm adapted to get into contact with a body portion outside the vagina, wherein the first arm and the second arm are provided for being connected with each other at their respective proximal end portion so as to form an essentially U- or V-shaped arrangement, characterized by coupling means adapted to provide a releasable connection of the first and second arms at their respective proximal end portion.

According to the present invention, both the first and second arms do not form an integral arrangement, but form separate parts which by the coupling means can be connected with each other or disconnected from each other. In the connected state of the first and second arms, the device according to the present invention can be used like a conventional "rabbit" stimulator with the first arm to be inserted into the vagina and the second arm to be brought into contact or touch outside with the skin of a portion of a female human body, in particular in the area of the clitoris or directly with said organ for stimulation. In the disconnected state, the first arm and the second arm each are provided as separate individual stimulation devices, wherein preferably the first arm can be used as a conventional dildo to be inserted into a sexual organ like the female vagina, whereas the second arm can be used as lay-on stimulator to be brought into contact or touch with or to be laid upon the skin of a certain portion of a human body for stimulation. So, the present invention provides a stimulation device which comprises a compact and integrated construction and has a threefold function for different types of stimulation so that the stimulation device can be used for different pleasure in accordance with the user's current needs and, thus, gives more fun. A further advantage of the present invention is that the user needs to buy only one stimulation device instead of three different stimulation devices and therefore to pay only for one stimulation device rather than for three ones so that the present invention results in the saving of costs.

Further advantageous embodiments and modifications of the present invention are defined in the dependent claims.

For a better handling, the proximal end portion of the second arm can be provided as a handle portion.

Further, the distal end portion of the second arm can comprise at least two fingers spaced from each other and arranged essentially side by side so that it has a shape in accordance with the "rabbit" style.

According to a further preferred embodiment, the first arm comprises a slightly curved shape wherein the curvature is oriented towards the second arm, when the first arm and second arms are connected with each other by the coupling means. Such a curved shape is advantageous for smoother insertion into the vagina and for the achievement of extra vaginal stimulation.

According to a still further preferred embodiment, the distal end portion of the second arm comprises a slightly curved shape wherein the curvature is oriented to the first arm when the first and second arms are connected with each other by the coupling means. According to a modification of this embodiment, the second arm comprises an S-shape. The provision of the second arm with a such curved shape brings more convenience to achieve optimal pleasure.

The length of the second arm can be shorter than the length of the first arm for a more advantageous consideration of the anatomy of a human, in particular female, body.

In order to better reach a pleasure point in different positions and for the user's individual current needs, the distal end portion of the second arm can be preferably flexible so that the distance of the distal end portion of the second arm to the first arm is variable.

In order to enhance stimulation, the second arm can preferably include a vibration means adapted to transfer vibrations to an outer surface of the second arm. According to a modification of this embodiment, the second arm includes a battery for supplying the vibration means with electrical power, and the proximal end portion of the second arm comprises an electrical connector for connection of an electrical cable for charging the battery. Preferably, the battery is located within the proximal end portion of the second arm, since usually the proximal end portion provides more space than the remaining portions of the second arm.

Instead of or in addition to the second arm, the first arm can be provided with a vibration means as well. In a preferred embodiment, the first arm includes a drive means adapted to subject the distal end portion of the first arm to rotational movements and/or to transfer vibrations to an second surface of the first arm. The rotation and/or vibration is advantageous for maximal stimulation.

According to a modification of the above embodiments, the coupling means comprises electrical connecting means adapted to provide an electrical connection, when the first and the second arms are connected with each other at their respective proximal end portion, so as to supply the drive means of the first arm with electrical power. This is advantageous in that the provision of a further battery in the first arm is not necessary.

According to a further preferred embodiment, the second arm comprises control means adapted to control the operation of the vibration means of the second arm and, when the first arm is connected with the second arm by the coupling means, to control the drive means of the first arm. In a modification of this embodiment, the control means comprises a control button provided at the outer surface of the proximal end portion of the second arm in order to provide a convenient access of the control means. The control button can be provided as a rocker switch. Alternatively, the control button is a cross-rocker switch comprising two pairs of opposite rocker switch elements, wherein both of the pairs of rocker switch elements are oriented at an angle, preferably a right angle, relative to each other so as to form a cross, wherein the one pair of rocker switch elements is provided for controlling the operation of the drive means of the first arm and the other pair of rocker switch elements is provided for controlling the operation of the vibration means of the second arm.

For a quick connection and a quick release in order to render the handling of the stimulation device more convenient, the coupling means preferably comprises a turn fastening means. According to a modification of this embodiment, the turn fastening means comprises a male engaging element provided at the one arm and a female engaging element formed in the other arm for accommodation of the male engaging element, wherein the engaging elements are provided so that the engaging elements can be loosely connected with each other or separated from each other when they are oriented at a first angular position relative to each other, and a tight engagement of the engaging elements with each other is generated when they are turned into a second angular position relative to each other. This embodiment of fastening means works like a bayonet lock and provides a very tight arrangement by a convenient handling. Further, the turn fastening means can comprise a knob which is provided so that the engaging elements are to be simply released from each other when the knob is pressed. Preferably, the knob can be mechanically coupled to the male engaging element.

In an alternative preferred embodiment, the coupling means comprises two fingers provided at the proximal end portion of the first arm and an engaging portion provided at the proximal end portion of the second arm, wherein the engaging portion is adapted to be accommodated within a cavity between the two fingers of the first arm and to be engaged with the fingers. So, the coupling means of this embodiment operates somewhat like a ‘docking station’ for the second arm whose proximal end is to be inserted between the two fingers at the proximal end portion of the first arm. This embodiment of the coupling means allows a quick connection and a quick release like a snap-lock and, thus, a very convenient handling, and further has a simple but effective construction which does not require high production costs.

According to a preferred modification of this embodiment, at each of both opposite sides the proximal end portion of the second arm comprises a concave recess so as to define a slim stem therebetween whose width is smaller than that of the remaining proximal end portion, wherein each of both the recesses is adapted to be engaged with a corresponding finger of the first arm.

According to a still further preferred modification, at least one of the fingers comprises a curved shape near its free end or at its free end so as to form a smooth nosed protrusion facing the other finger, and the engaging portion of the second arm comprises a concave recess for accommodating and engaging the protrusion of the finger.

For a still better engagement, according to a further modification of the aforementioned embodiment, the proximal end portion of the second arm comprises an edge which has essentially a U-shape and surrounds the engaging portion so that the open end of the “U” is essentially oriented towards the distal end portion of the second arm. This construction has the advantage to lock the second arm against an undesired tilting movement relative to the first arm.

In an alternative preferred embodiment, the proximal end portion of the second arm comprises a convex connecting portion formed like a bulge, and the proximal end portion of the first arm comprises a concave connecting portion formed like a well, depression or hollow and adapted to accommodate the convex connecting portion of the second arm when the first and second arms are connected to each other by the coupling means.

Preferably, the surface of the first arm and/or the second arm at least partly comprises soft silicone material, since such a material has the advantage to be soft, flexible and hygienic.

In the following, preferred embodiments according to the present invention will be described with reference to the accompanying drawings in which.

Figure 1:
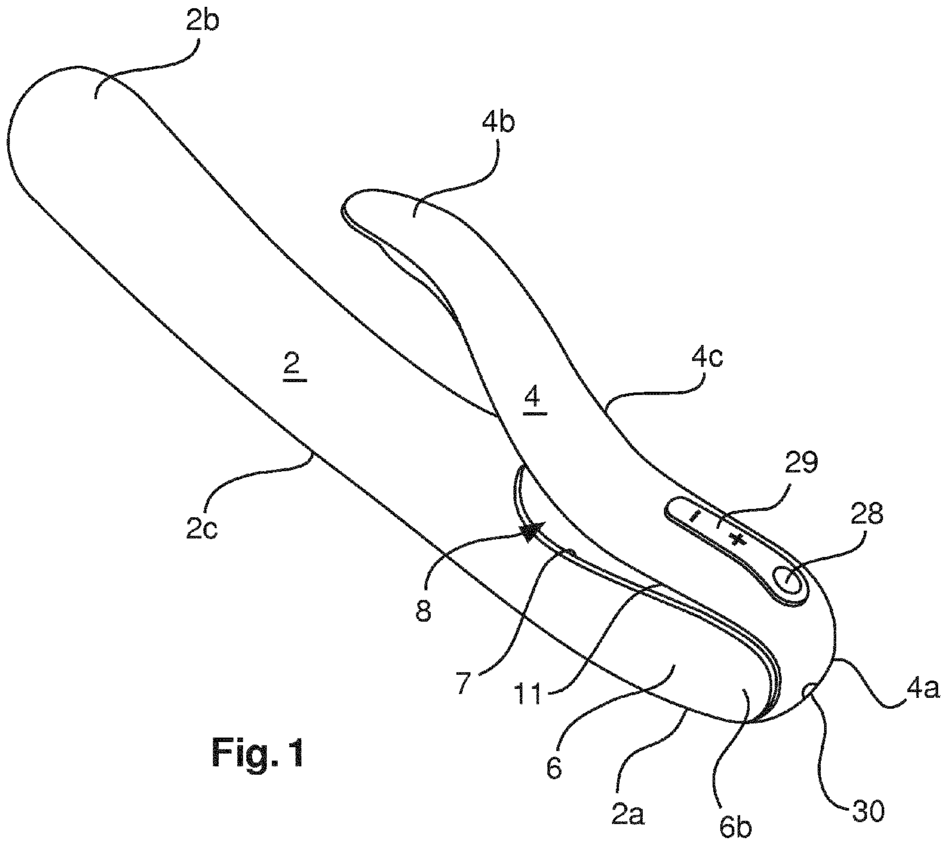
FIG. 1 is a perspective view of a stimulation device according to a first preferred embodiment of the present invention in a first operational mode with both arms being connected with each other for use as a “rabbit” vibrator.
Figure 2:
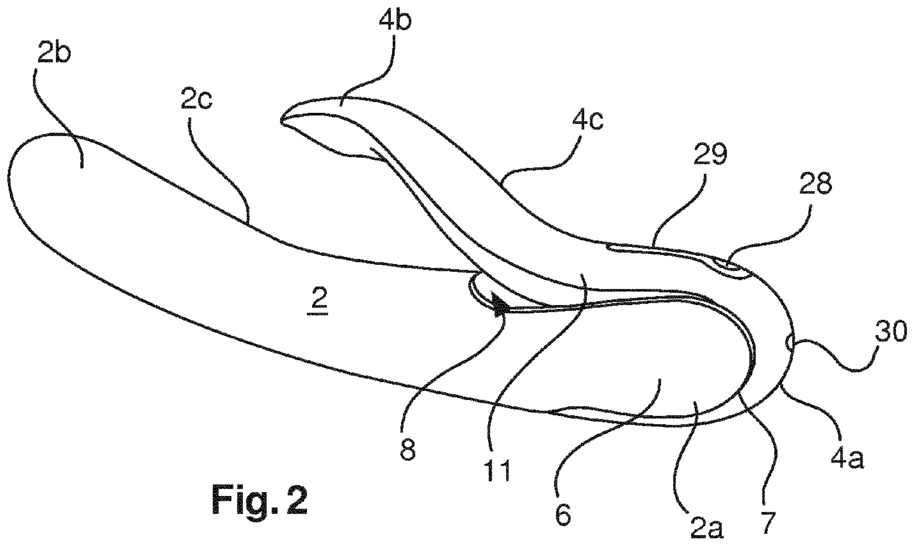
FIG. 2 is a perspective side view of the device of FIG. 1 in the operational mode.

FIGS. 1 to 5 show a stimulation device according to a first preferred embodiment of the present invention. The device comprises an elongated first arm 2 having a proximal end portion 2*a*, a distal end portion 2*b* and an elongated middle section 2*c* between the proximal end portion 2*a* and the distal end portion 2*b*, and a second arm 4 having a proximal end portion 4*a*, a distal end portion 4*b* and an elongated middle section 4*c* between the proximal end portion 4*a* and the distal end portion 4*b*. In a first operational mode as shown in FIGS. 1 and 2, both the first and second arms 2, 4 are connected with each other at their respective proximal end portion 2*a*, 4*a* so as to form an essentially V-shaped arrangement wherein the first and second arms 2, 4 are oriented essentially in the same direction and the distal end portions 2*b*, 4*b* of the arms 2, 4 are spaced from each other. However, both the arms 2, 4 can alternatively be formed and/or the connection of the arms 2, 4 at their respective proximal end portion 2*a*, 4*a* can alternatively be provided so as to form any other arrangement, provided the distal end portions 2*b*, 4*b* of the arms 2, 4 are spaced from each other, e.g. like an essentially U-shaped arrangement.

In a first operational mode as shown in FIGS. 1 and 2, wherein the first and second arms 2, 4 are in the connected state, the device can be used like a conventional "rabbit" stimulator with the first arm 2 at its distal end portion 2*b* to be inserted into the vagina and the second arm 4 to be brought into contact or touch outside with the skin of a portion of a female human body, in particular in the region of the clitoris or directly with said organ for stimulation. Therefore, the first arm 2 can also be called "inner" arm, and the second arm 4 can also be called "outer" arm.

As particularly shown in FIGS. 1 and 2 the first arm 2 comprises a slightly curved shape wherein the curvature is oriented towards the second arm 4 in the aforementioned first operational mode, which is advantageous for smoother insertion into the vagina and for the achievement of extra stimulation. As also particularly shown in FIGS. 1 and 2, the second arm 4 comprises a slight S-shape wherein the curvature of its distal end portion 4*b* is slightly oriented to the first arm 2 in the aforementioned first operational mode, which results in more convenience to achieve optimal pleasure.

As further shown in the FIGS. 1 to 5, the length of the second arm 4 is shorter than the length of the first arm 2.

For a better "rabbit" function in the first operational mode according to FIGS. 1 and 2 in order to better reach a pleasure point in different positions in accordance with the user's individual current needs, the distal end portion 4*b* of the second arm 4 is flexible so that the distance of the distal end portion 4*b* of the second arm 4 to the first arm 2 is variable.

The surface of the first arm 2 and/or the second arm 4 at least partly comprises soft silicone material.

Figure 3:
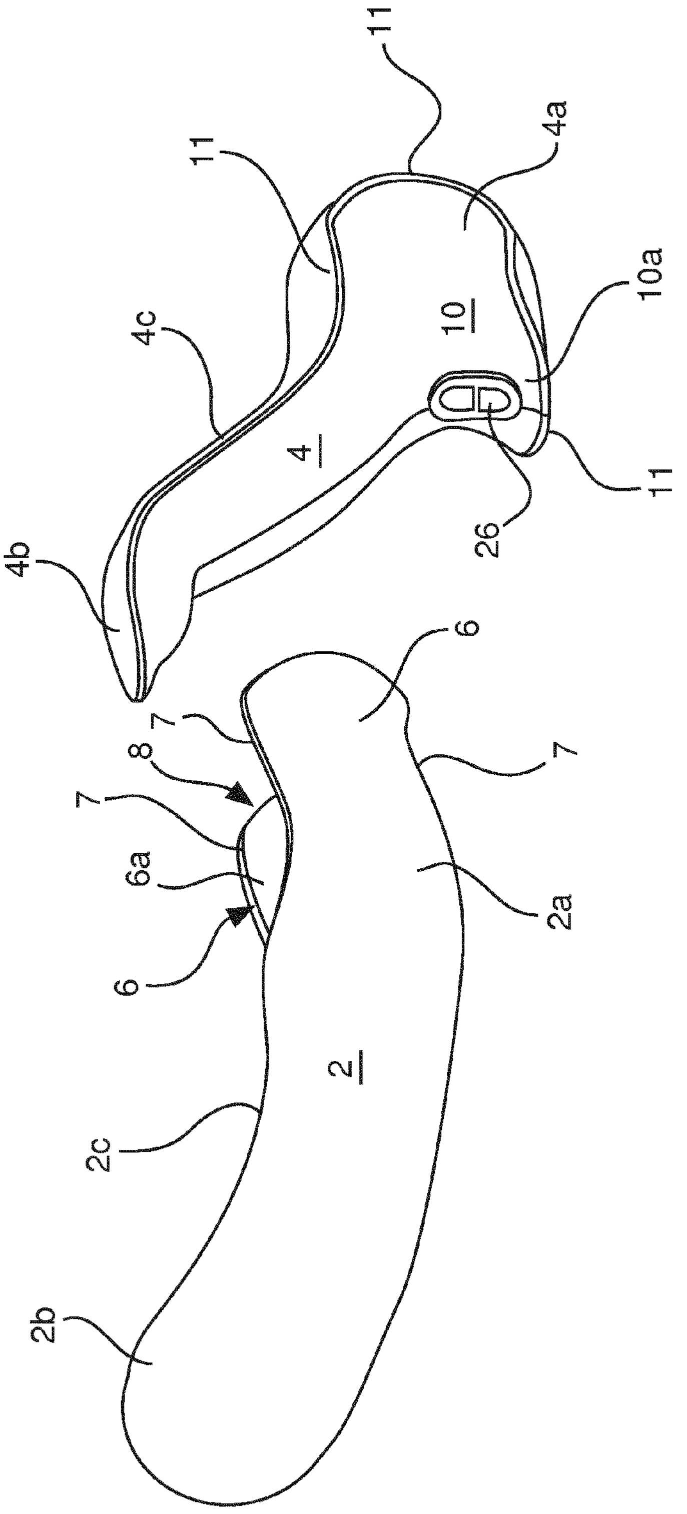
FIG. 3 is another perspective side view of the device of FIG. 1 in a second operational mode with both the arms being released from each other for separate different use.
Figure 4:
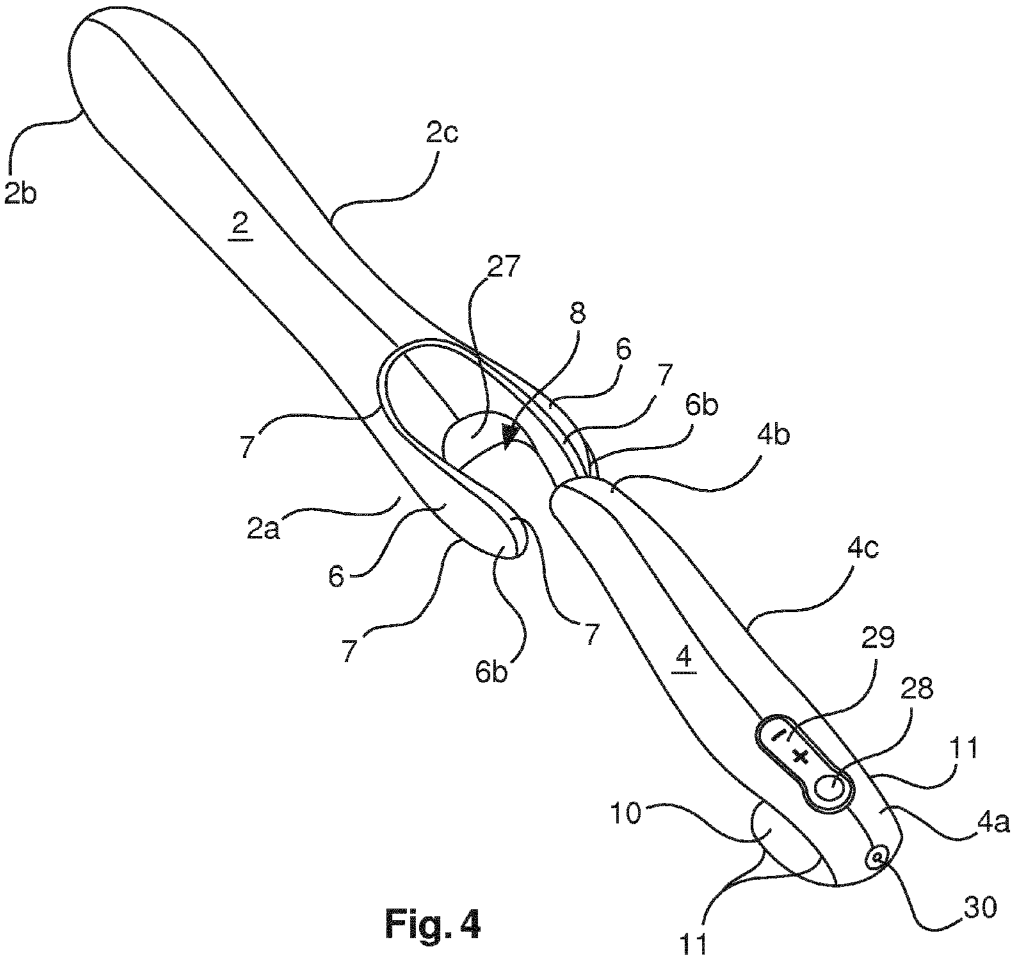
FIG. 4 is another perspective side view of the device of FIG. 1 in the second operational mode according to FIG. 3.

The connection of the first and second arms 2, 4 is releasable so that in the disconnected state the first arm 2 and the second arm 4 each are provided as separate individual stimulation devices. Consequently, in addition to the first operational mode according to the FIGS. 1 and 2, there is a second operational mode which is shown in FIGS. 3 and 4, wherein the device is divided into two separate individual stimulation devices each formed by one of the first and second arms 2, 4. For instance, in the second operational mode the first arm can be used as a conventional dildo to be inserted into a sexual organ, whereas the second arm 4 can be used as lay-on stimulator to be brought into contact or touch or to be laid upon the skin of a certain portion of a human body for stimulation.

For the releasable connection of the first and second arms 2, 4 with each other, there are provided suitable coupling means.

In the embodiment according to FIGS. 1 to 5, the coupling means comprises two fingers 6 which form the proximal end portion 2*a* of the first arm 2 and are surrounded by an edge 7 which defines a boundary for the fingers 6. As particularly shown in FIGS. 3 and 4, both the fingers 6 are spaced from each other so that an open cavity 8 is provided between inner surfaces 6*a* of the fingers 6. As particularly shown in FIG. 4, the free end 6*b* of each finger 6 comprises a smooth nosed protrusion facing the other finger 6 whereby the entrance of the cavity 8 between the free ends 6*b* of the fingers 6 is slightly restricted.

The coupling means further comprises an engaging portion 10 provided at the proximal end portion 4*a* of the second arm 4. The shape of the engaging portion 10 is essentially complimentary with regard to the shape of the cavity 8. The proximal end portion 4*a* of the second arm 4 comprises an edge 11 which has essentially a U-shape and surrounds the engaging portion 10 so that the open end of the "U" is essentially oriented towards the distal end portion 4*b* of the second arm 4. Due to its complementary shape, the engaging portion 10 at the proximal end portion 4*a* of the second arm 4 is adapted to be accommodated within the cavity 8 between the two fingers 6 of the proximal end portion 2*a* of the first arm 2. With regard to the smooth nosed protrusion at the inner surface 6*a* of the free end 6*b* of the fingers 6, in a complementary manner the engaging portion 10 at the proximal end portion 4*a* of the second finger 4 comprises a corresponding concave recess for accommodating said protrusion of the finger 6 so that a face section 10*a* of the engaging portion 10 facing the first arm 2 in the connected state and the first operation mode is wider than the remaining engaging portion 10. In order to be able to insert the engaging portion 10 of the second arm 4 with its wider face section 10*a* through the constricted entrance of the cavity 8 in the proximal end portion 2*a* of the first arm 2, the fingers 6 of the first arm 2 are elastic, in particular by being made of elastic material. Additionally or alternatively, the engaging portion 10 at the proximal end portion 4*a* of the second arm 4 can be made of elastic material at least at its surface.

So, in the connected state or first operational mode, as shown in FIGS. 1 and 2, the fingers 6 with its convex inner surface 6*a* fit with the concave engaging portion 10 wherein the edge 7 surrounding the fingers 6 and the edge 11 surrounding the engaging portion 10 are essentially in contact with each other. Not only due to the complementary compliance or similarity between the shape of the inner surface 6*a* of the fingers 6 and the shape of the engaging portion 10, but also due to the elasticity of the fingers 6 and/or the engaging portion 10, the fingers 6 can be brought into tight engagement with the engaging portion 10 so as to obtain a fix connection between the first arm 2 and the second arm 4. So, the coupling means according to the above described embodiment operates like a snap-lock allowing a quick connection and a quick release.

Figure 5:
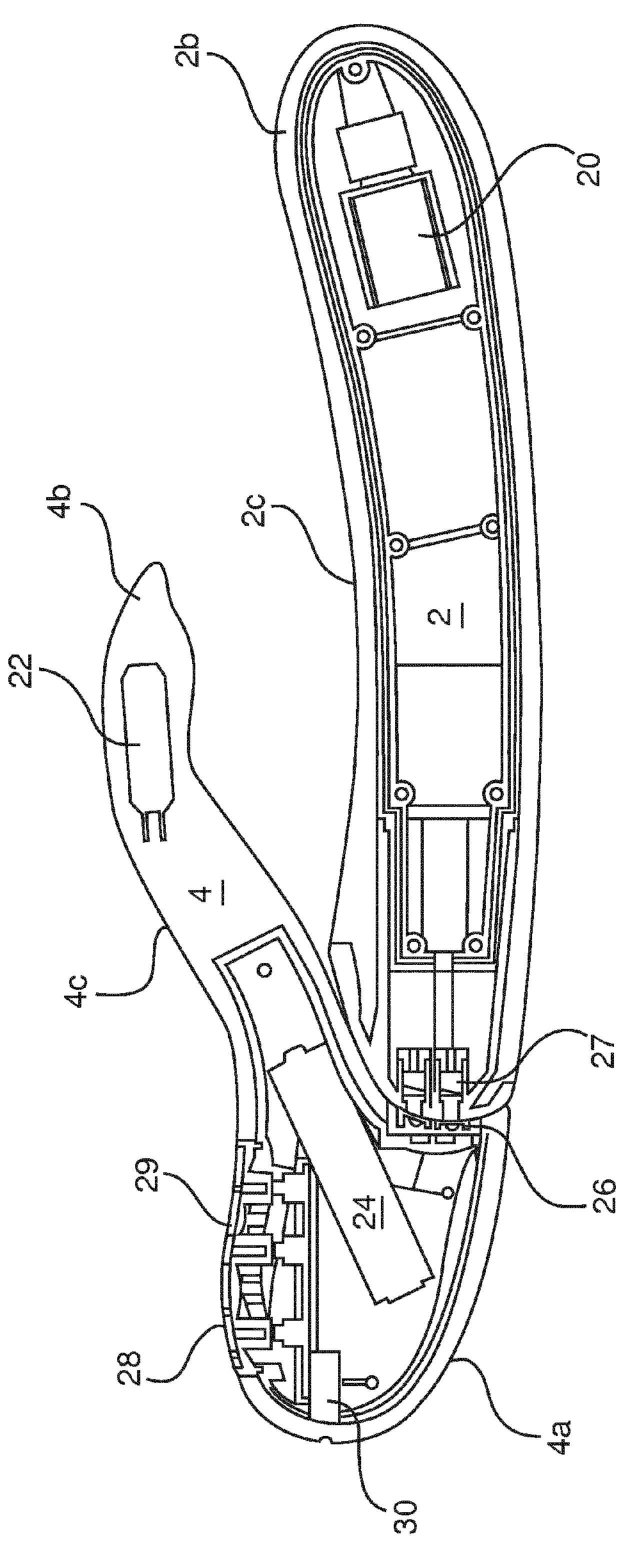
FIG. 5 is a longitudinal section through the device of FIG. 1 in its first operational mode with both the arms being connected with each other.

In order to enhance stimulation, the first arm 2 includes a first vibration means 20 and the second arm 4 includes a second vibration means 22, as schematically shown in FIG. 5. In the shown embodiment, the first vibration means 20 is arranged within the distal end portion 2*b* of the first arm 2 and preferably comprises a rotation ball head driven by a rotation motor (not shown) in order to subject the distal end portion 2*b* of the first arm 2 not only to vibrations but also to a rotational movement for maximal stimulation. The vibration means 20 may be further adapted to subject the elongated middle section 2*c* of the first arm to vibrations for a stimulation of the vaginal canal or lips; alternatively, for this purpose a further separate vibration means may be arranged within the first arm 2 and in particular its elongated middle section 2*c*. In the embodiment shown in FIG. 5, the vibration means 22 is located within the distal end portion 4*b* of the second arm 4 and provided as a vibration motor in order to create vibrations subject to the distal end portion 4*b* of the second arm 4 for an intensive feeling of clitoral pleasure. For supplying the vibration means 22 with electrical power, the second arm 4 further includes a battery 24 which is arranged essentially in the region of the proximal end portion 4*a*. In the embodiment shown in FIG. 5, the first arm 2 does not include a battery, but the vibration means 20 is supplied with electrical power from the battery 24 in the second arm 4 via electrical connectors 26, 27. As shown in FIGS. 3 to 5, a first electrical connector 26 is provided at the face section 10*a* of the engaging portion 10 of the second arm 4 facing the first arm 2 (cf. FIG. 3), and the second electrical connector 27 is arranged at a distal portion of the inner surface of the cavity 8 (cf. FIG. 4). The electrical connectors 26, 27 are provided and located so that they are in electrical contact with each other when the first and second arms 2, 4 are mechanically connected with each other by means of the above described coupling means.

Not only the battery 24 but also a (not shown) control unit is arranged within the second arm 4 only so that not only electrical power, but also control signals from said control unit are transferred via the electrical connector 26, 27 to the vibration means 20 in the first arm 2. For activating and deactivating the vibrations means 20, 22 and controlling the control unit, switches are provided whose buttons 28, 29 are arranged, in the embodiment shown FIGS. 1 to 5, at an outer side of the proximal end portion 4*a* of the second arm 4, wherein the first button 28 is a program button for selecting a certain vibration program and the second button 29 is an intensity button for adjusting the intensity of the vibrations. In particular due to the arrangement of the buttons 28, 29 in the shown embodiment, the proximal end portion 4*a* of the second arm 4 is preferably used as a handle portion. For connection of an electrical cable for charging the battery 24, a further electrical connector 30 is provided at the free end of the proximal end portion 4*a* of the second arm 4.

Figure 6:
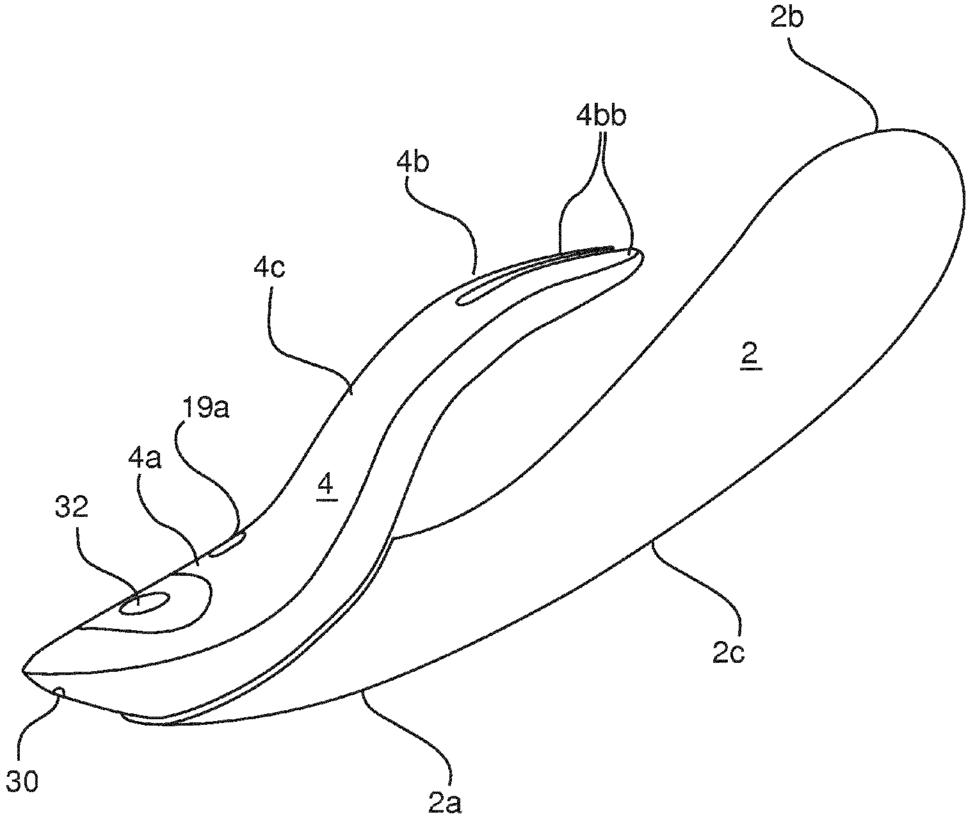
FIG. 6 is a perspective view of a stimulation device according to a second preferred embodiment of the present invention in its first operational mode with both arms being connected with each other for use as a “rabbit” vibrator.
Figure 7:
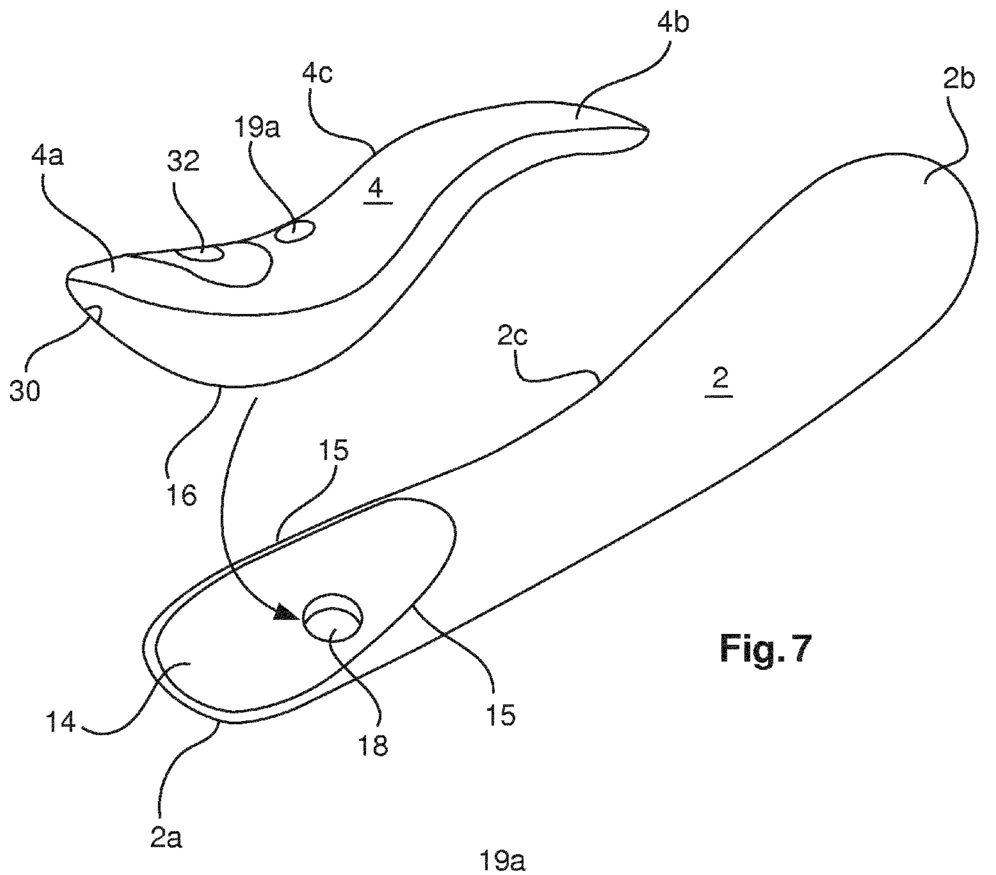
FIG. 7 is a perspective view of the device of FIG. 6 in its second operational mode with both the arms being released from each other for separate different use.
Figure 8:
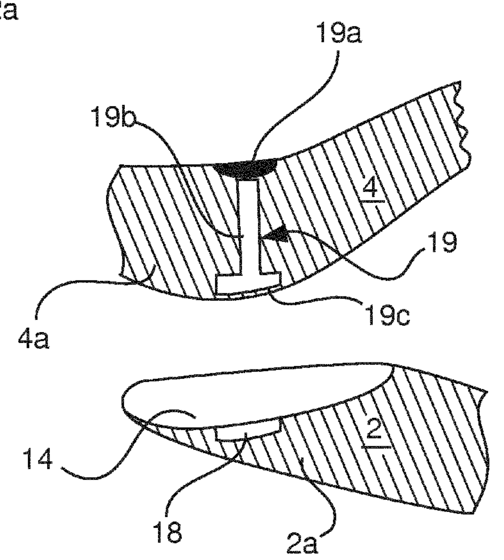
FIG. 8 a longitudinal section through a portion of the device of FIG. 6 in its second operational mode according to FIG. 7 in order to schematically show the coupling means.

FIGS. 6 to 8 show a second embodiment of the stimulation device wherein the similar or same elements already included in the first embodiment are denoted with the same reference numerals as in the FIGS. 1 to 5. In order to avoid a repetition of a description of those embodiments which are already included in the first embodiment with reference to FIGS. 1 to 5, in the following only those elements are described which differ from the first embodiment.

In contrast to the first embodiment, in the second embodiment the distal end portion 4*b* of the second arm 4 comprises two fingers 4*bb* spaced from each other so as to look as a pair of "rabbit" ears, as particularly shown in FIG. 6.

A further more important difference from the first embodiment regards the connection between the first and second arm 2, 4. As particularly shown in FIG. 7 the proximal end portion 2*a* of the first arm 2 a comprises a concave connecting portion 14 formed like well, depression or hollow, and the proximal end portion 4*a* of the second arm 4 comprises a convex connecting portion 16 formed like a bulge and adapted to be inserted into the concave connection portion 14 of the first arm 2. For an essentially flat arrangement the shape of the concave connecting portion 14 of the first arm 2 is essentially complementary with regard to the shape of the convex connecting portion 16 of the second arm 4 so as to obtain an optimum fit of the convex connecting portion 16 in the concave connecting portion 14 when the first and second arms 2, 4 are connected to each other in the first operational mode or connecting state as shown in FIG. 6. As further shown in FIG. 7, the concave connection portion 14 at the proximal end portion 2*a* of the first am 2 is surrounded and limited by an endless edge 15 which is positioned close to the surface of the convex connecting portion 16 when the first and second arm 2, 4 are connected which each other in the first operational mode (cf. FIG. 6).

Moreover, the second embodiment according to the FIGS. 6 to 8 differs from the first embodiment according to the FIGS. 1 to 5 in the construction of the coupling means which are embodied as a rotational fastening means and in particular a quarter-turn fastener. As seen from the FIGS. 7 and 8, an engaging hole 18 is arranged in the bottom of the concave connecting portion 14 of the proximal end portion 2*a* of the first arm 2 wherein this engaging hole 18 is provided as a female engaging element. As further seen from FIG. 8, the proximal end portion of the second arm 4 includes coupling element 19 comprising a knob 19*a* at the outer surface of the second arm 4, a stem 19*b* extending through the second arm 4 and a male engaging element 19*c* provided at the surface of the connecting portion 16. The knob 19*a*, the stem 19*b* and the male engaging element 19*c* are coupled and cooperate with each other so that, with the convex connecting portion 16 being arranged within the concave connecting portion 14 for connection of the first and second arm 2, 4 with each other, the male engaging element 19*c* oriented at a first angular position can loosely inserted into and connected with hole 18 and due to pressing of the knob 19*a* the pressing force is transferred via the stem 19*b* and changed to a rotational movement so that the male engaging element 19*c* is turned to a second angular position where the male engaging element 19*c* is in tight engagement with the hole 18. A further pressing of the knob 19*a* again results in turning the male engaging element 19*c* in a reverse direction for releasing from the hole 18 in order to disconnect the first and second arms 2, 4 from each other.

As further shown in FIGS. 6 and 7, instead of the two buttons of the first embedment, the second embodiment comprises a control button 32 which is located at the outer surface of the proximal end portion 4*a* of the second arm 4, but is provided as a circular cross rocker switch comprising a central switch element and two pairs of opposite rocker switch elements which are not denoted by reference numerals here, wherein both of the pairs of rocker switch elements are oriented at a right angle relative to each other so as to form a cross, wherein the one pair of rocker switch elements is provided for controlling the operation of the vibration means of the first arm 2 and the other pair of rocker switch elements is provided for controlling the operation of the vibration means of the second arm 4, whereas the central button is provided for selecting and changing programs for both the vibration means.

The invention claimed is:

1. A stimulation device comprising:

a first arm having a first proximal end portion and a distal end portion adapted to be inserted into a vagina; and a second arm having a proximal end portion and a distal end portion adapted to contact a body portion outside the vagina, wherein the first arm and the second arm are adapted to be connected with each other at their respective proximal end portion so as to form an essentially U- or V-shaped arrangement; and coupling means for releasably connecting the first and second arms at their respective proximal end portions;

wherein the first arm comprises a curved shape wherein the curvature is oriented towards the second arm when the first and second arms are connected with each other by the coupling means.

2. The device according to claim 1 wherein the distal end portion of the second arm comprises a curved shape wherein the curvature is oriented towards the first arm when the first and second arms are connected with each other by the coupling means.

3. The device according to claim 2, wherein the second arm comprises an S-shape.

4. The device according to claim 1, wherein the distal end portion of the second arm is flexible so that the distance of the distal end portion of the second arm to the first arm is variable.

5. The device according to claim 1 wherein the second arm includes a vibration means adapted to transfer vibrations to an outer surface of the second arm.

6. The device according to claim 5, wherein the second arm includes a battery for supplying the vibration means with electrical power, and the proximal end portion of the second arm comprises an electrical connector for connection of an electrical cable for charging the battery.

7. The device according to claim 6, wherein the battery is located within the proximal end portion of the second arm.

8. The device according to claim 1, wherein the first arm includes a drive means for transferring vibrations to an outer surface of the first arm and/or to subject the distal end portion of the first arm to rotational movements.

9. The device according to claim 8, wherein the coupling means comprises an electrical connector adapted to provide an electrical connection when the first and the second arms are connected with each other at their respective proximal end portions, so as to supply the drive means of the first arm with electrical power.

10. The device according to claim 9, wherein the second arm comprises control means adapted to control the operation of the vibration means of the second arm and, when the first arm is connected with the second arm by the coupling means, to control the drive means of the first arm.

11. The device according to claim 10, wherein the control means comprises a control button provided at the outer surface of the proximal end portion of the second arm.

12. The device according to claim 11, wherein the control button comprises a cross rocker switch comprising two pairs of opposite rocker switch elements, wherein both of the pairs of rocker switch elements are oriented at an angle, preferably a right angle, relative to each other so as to form a cross, wherein the one pair of rocker switch elements is provided for controlling the operation of the drive means of the first arm and the other pair of rocker switch elements is provided for controlling the operation of the vibration means of the second arm.

13. The device according to claim 1, wherein the coupling means comprises a rotational fastener.

14. The device according to claim 13, wherein the rotational fastener comprises a male engaging element provided at one arm and a female engaging element formed in the other arm for accommodation of the male engaging element, wherein the engaging elements are provided so that they can be loosely connected with each other or separated from each other when they are oriented at a first angular position relative to each other, and the engaging elements can be in tight engagement with each other when they are turned into a second angular position relative to each other.

15. The device according to claim 14, wherein the rotational fastener comprises a knob which is provided so that the engaging elements can be released from each other when the knob is pressed.

16. The device according to claim 15, wherein the knob is mechanically coupled to the male engaging element.

17. The device according to claim 1, wherein the coupling means comprises two fingers provided at the proximal end portion of the first arm and an engaging portion provided at the proximal end portion of the second arm, wherein the engaging portion can be accommodated within a cavity between the two fingers of the first arm and engaged with the fingers.

18. The device according to claim 17, wherein opposing sides of the proximal end portion of the second arm each comprise a concave recess so as to define a slim stem therebetween whose width is smaller than that of the remaining proximal end portion of the second arm, wherein each of the recesses is adapted to be engaged with a corresponding finger of the first arm.

19. The device according to claim 17, wherein at least one of the fingers comprises a curved shape near its free end or at its free end so as to form a smooth nosed protrusion facing the other finger, and the engaging portion of the second arm comprises a concave recess for accommodating and engaging the protrusion of the finger.

20. The device according to claim 17 wherein the proximal end portion of the second arm comprises an edge which has essentially a U-shape and surrounds the engaging portion so that the open end of the "U" is essentially oriented towards the distal end portion of the second arm.

21. The device according to claim 1, wherein the proximal end portion of the second arm comprises a convex connecting portion formed like a bulge, and the proximal end portion of the first arm comprises a concave connecting portion formed like a well, depression or hollow and adapted to accommodate the convex connecting portion of the second arm when the first and second arms are connected to each other by the coupling means.

22. The device according to claim 1, wherein the surface of the first arm or the second arm at least partly comprises soft silicone material.

23. A stimulation device comprising:

a first arm having a proximal end portion and a distal end portion adapted to be inserted into a vagina;

a second arm having a proximal end portion and a distal end portion adapted to contact a body portion outside the vagina, wherein the first arm and the second arm are adapted to be connected with each other at their respective proximal end portions so as to form an essentially U- or V-shaped arrangement and wherein the second arm comprises an S-shape; and coupling means for releasably connecting the first and second arms at their respective proximal end portions;

wherein the distal end portion of the second arm is flexible so that the distance from the distal end portion of the second arm to the first arm is variable.

24. The device according to claim 23, wherein the second arm includes vibration means for transfer vibrations to an outer surface of the second arm.

25. The device according to claim 23, wherein the coupling means comprises a rotational fastener.

26. The device according to claim 23 wherein the surface of at least one of the first arm and the second arm at least partly comprises a soft silicone material.

27. The device according to claim 23 wherein the coupling means comprises two fingers provided at the proximal end portion of the first arm and an engaging portion provided at the proximal end portion of the second arm, wherein the engaging portion can be accommodated within a cavity between the two fingers of the first arm and engaged with the fingers.

* * * * *